United States Patent
Wang

(10) Patent No.: US 7,147,607 B2
(45) Date of Patent: Dec. 12, 2006

(54) TRANSENDOSCOPIC DOUBLE NEEDLE ASSEMBLY

(76) Inventor: Ko-Pen Wang, 14525 Falls Rd., Butler, MD (US) 21023

( * ) Notice: Subject to any disclaimer, the term of this patent is extended or adjusted under 35 U.S.C. 154(b) by 373 days.

(21) Appl. No.: 10/693,645

(22) Filed: Oct. 27, 2003

(65) Prior Publication Data

US 2005/0090763 A1   Apr. 28, 2005

(51) Int. Cl.
*A61B 10/00* (2006.01)
*A61B 17/32* (2006.01)
(52) U.S. Cl. .................... 600/566; 600/564; 606/170
(58) Field of Classification Search ............ 600/562, 600/564–567, 569–571; 604/33, 40, 42, 604/117, 164.08, 523; 606/167, 170
See application file for complete search history.

(56) References Cited

U.S. PATENT DOCUMENTS

| | | | |
|---|---|---|---|
| 4,249,541 A | 2/1981 | Pratt | |
| 4,532,935 A | 8/1985 | Wang | |
| 4,617,940 A | 10/1986 | Wang | |
| 4,693,257 A * | 9/1987 | Markham | 600/565 |
| 4,702,260 A | 10/1987 | Wang | |
| 4,766,906 A | 8/1988 | Wang | |
| 4,791,937 A | 12/1988 | Wang | |
| 4,890,626 A | 1/1990 | Wang | |
| 4,966,162 A | 10/1990 | Wang | |
| 5,056,529 A * | 10/1991 | de Groot | 600/567 |
| 5,320,110 A | 6/1994 | Wang | |
| 5,394,887 A * | 3/1995 | Haaga | 600/567 |
| 5,601,588 A * | 2/1997 | Tonomura et al. | 606/185 |
| 6,022,363 A * | 2/2000 | Walker et al. | 606/159 |
| 6,110,127 A * | 8/2000 | Suzuki | 600/565 |
| 6,514,215 B1 * | 2/2003 | Ouchi | 600/564 |

* cited by examiner

*Primary Examiner*—Max F. Hindenburg
*Assistant Examiner*—Michael Apanius
(74) *Attorney, Agent, or Firm*—Davidson Berquist Jackson & Gowdey, LLP

(57) ABSTRACT

A medical device for obtaining biopsy tissue samples is provided includes a flexible outer tubular member having proximal and distal ends, and an inner tubular member slidably and coaxially received within the outer tubular member and a stylet slidably and coaxially received within the inner tubular member. A spring member coaxially oriented about the stylet has a proximal end attached to the stylet and a distal end attached to an outer hollow needle member. The inner hollow needle is attached to the distal end of the stylet to effect reciprocal movement thereof. The device has a retracted position, a first extended position wherein the outer hollow needle and a first portion of the inner needle are deployed beyond the distal end of the device, and a second extended position wherein a second length of the inner needle is deployed beyond the distal end of the device.

25 Claims, 8 Drawing Sheets

TRANSENDOSCOPIC DOUBLE NEEDLE ASSEMBLY

FIELD OF THE INVENTION

This invention relates generally to a transendoscopic needle assembly for use with a flexible bronchoscope, endoscope or any other type of body cavity scope and more particularly to an improved transendoscopic needle assembly for obtaining a tissue sample from within the body.

BACKGROUND OF THE INVENTION

Conventionally, when biopsies were desired to be taken of the lymph nodes, for example, to aid in the diagnosis of carcinoma, the prior techniques would typically utilize a substantially rigid needle and penetrate the body via percutaneous entry. For example, U.S. Pat. Nos. 3,630,192 and 3,628,524 each to Jamshidi disclose biopsy needles suitable for percutaneous entry. More recently, less invasive flexible biopsy instruments which do not require percutaneous entry have been described. U.S. Pat. No. 4,249,541 to Pratt discloses that a flexible biopsy instrument can be utilized in combination with a fiberoptic bronchoscope.

U.S. Pat. No. 4,617,940 to Wang, the entirety of which is incorporated herein by reference, describes a completely flexible bronchoscopic needle assembly wherein relatively non-invasive biopsy procedures can be performed utilizing the needle in combination with a fiberoptic bronchoscope. The attending physician inserts the bronchoscope into a predetermined one of the patient's natural orifices depending upon the particular organ desired to be biopsied. The needle assembly, which includes an outer catheter and an inner coaxial stylus attached to a retractable needle, is slideably inserted into a receiving passageway of the bronchoscope. The needle is urged into the tissue of the patient by a stabbing force exerted on the proximal end of the stylus (e.g. the end on the exterior of the patient's body) after the outer catheter comes into the bronchoscope's field of view. The bronchoscope enables the attending physician to accurately position the needle and to penetrate the exact location of the desired organ due to the viewing capabilities provided thereby.

A particular problem in utilizing a flexible bronchoscopic needle is that the needle assembly must be flexible enough to allow the physician to maneuver the assembly through the patient's orifice to the target site, but rigid enough to allow penetration of the collection device, such as a needle, into the target tissue. The bronchial wall or hard tumor tissue will need to be penetrated and thus may present significant resistance to entry of the needle. Upon arrival at the target site, the needle assembly, particularly the distal portion of the needle assembly, should be rigid enough to provide a countering pressure against the resistance provided by the bronchial wall or hard tumor tissue or both together. Conventional needle assemblies have not provided a satisfactory means for balancing the necessary flexibility with the desired rigidity as the needle is extended into the target tissue. Thus, a need exists for a needle assembly having flexible characteristics as the assembly is maneuvered through a patient's orifice while having rigid characteristics as the needle is inserted into the target tissue.

When obtaining a biopsy of a patient's tissue, it is often desirable for the brochoscopic needle to penetrate the target site in a perpendicular direction to minimize the length of the penetration into the patents' tissue, and to reduce patient healing time. Another problem with conventional bronchoscopic needles is that the length of the needle may hinder the ability of the needle to enter a target site in a direction perpendicular to the target site wall because the length of conventional needles limits the flexibility of the distal end of conventional flexible bronchoscopic needle assemblies. Thus, a need also exists for a needle assembly having the ability to appropriately penetrate a target site wall in a direction substantially perpendicular to the target site wall.

SUMMARY OF THE INVENTION

The present invention provides a flexible endoscopic biopsy sampling device which has a telescopic needle assembly. By providing a telescopic needle assembly, which optionally has a retracted length that is shorter than conventional needle assemblies, the present medical device can be more flexible than conventional devices. As a result, the inventive device is more easily maneuvered through a patient's orifice while having the desired rigid characteristics as the needle is telescopically extended and inserted into the patient's target tissue. Additionally, by providing a telescopic needle assembly, which optionally has a retracted length that is shorter than conventional needle assemblies, the present invention provides a medical device having the ability to penetrate a target site wall in a direction substantially perpendicular to the target site wall.

In one embodiment, the present invention is directed to a medical device which includes a flexible outer tubular member having proximal and distal ends. An inner tubular member having proximal and distal ends is slidably and coaxially received within the outer tubular member, and a flexible inner stylet having proximal and distal ends is slidably and coaxially received within the inner tubular member. A spring member is provided having proximal and distal ends and which is oriented adjacent the distal end of the outer tubular member. The spring member is coaxially received within the outer tubular member and surrounds a portion of the inner stylet, and the proximal end of the spring member is coupled to the stylet. A retractable outer hollow needle member having a proximal end is coupled to the distal end of the spring member. The device also includes a retractable inner hollow needle member slidably and coaxially received within the outer hollow needle member and having a proximal end coupled to the distal end of the stylet. Preferably, the inner tubular member is attached to a first grippable cap member, and the stylet is attached to a second grippable cap member. Optionally, the inner hollow needle member includes a side gap which includes trocar edge.

In this embodiment, the device includes a retracted position wherein the inner and outer hollow needle members are completely housed within the outer tubular member, a first extended position wherein the outer hollow needle member and a first length of the inner hollow needle member extend beyond the distal end of the outer tubular member, and a second extended position wherein the outer hollow needle member and a second length of the inner hollow needle member extend beyond the distal end of the outer tubular member, the second length being longer than the first length. Optionally, the spring member is more compressed in the second extended position than in the first extended position. The device preferably includes a hard tip rigidly fixed to the distal end of the outer tubular member, the tip including a bearing surface on the proximal end thereof. Optionally, the outer hollow needle member includes a limiting member rigidly associated with the outer hollow needle member and contacting the bearing surface of the tip member in the first and second extended positions.

Optionally, the spring member comprises a first spring having proximal and distal ends and a second spring having proximal and distal ends, and wherein the first spring is oriented distally with respect to the second spring, and wherein the distal end of the first spring is attached to the outer hollow needle member, and the proximal end of the second spring is attached to the stylet. The first spring may have a first wavelength and the second spring may have a second wavelength that is greater than or less than the first wavelength in the first extended position The second spring also preferably includes a third wavelength in the second extended position, which is less than the second wavelength.

In another embodiment, the invention is directed to a tissue collection device, which includes an elongated outer flexible hollow catheter having proximal and distal ends, and a rigid inner tubular member slidably positioned within the proximal end of the hollow catheter. An elongated stylet is slidably positioned within the rigid inner tubular member and a helically wound wire member having proximal and distal ends is coaxially attached to the stylet. The device also includes an outer hollow needle member attached to the distal end of the helically wound wire member, and an inner hollow needle member telescopically received within the outer hollow needle member, wherein the inner hollow needle member includes a sampling device, e.g., a conventional needle or a closed-off needle with a side gap having a sharp trocar edge.

Optionally, the wire member has a proximal region having a first wavelength, and a distal region having a second wavelength, the second wavelength normally being longer than or, alternatively, shorter than the first wavelength. The device preferably includes a retracted position wherein the sampling device is housed within the catheter, a first extended position wherein a first length of the inner hollow needle member extends beyond the distal end of the catheter, and a second extended position wherein a second length of the inner hollow needle member extends beyond the distal end of the catheter, wherein the second length is longer than the first length.

In another embodiment, the present invention is directed to a medical device, which includes a leur lock member having first and second grippable cap members, wherein the leur lock member is connectable to an aspirating device. The device also includes an outer tubular member having proximal and distal ends, the proximal end being connected to the leur lock mechanism. A rigid inner tubular member having proximal and distal ends is slidably positioned within the proximal end of the outer tubular member. The proximal end of the inner tubular member is attached to the first grippable cap member. An elongated stylet is also provided having proximal and distal ends and being slidably positioned within the rigid inner tubular member. The proximal end of the stylet is attached to the second grippable cap member. A compressable spring member having proximal and distal ends coaxially surrounds a portion of the stylet, wherein the proximal end of the spring member is attached to the stylet. An outer hollow needle member having a proximal end which is attached to the distal end of the spring member. The invention also includes an inner hollow needle member having proximal and distal ends and being telescopically received within the outer hollow needle member, wherein the proximal end of the inner hollow needle member is attached to the distal end of the stylet.

Preferably, the device includes a retracted position wherein the outer and inner hollow needle members are housed within the outer tubular member; a first extended position, wherein a first portion of the inner hollow needle member extends distally beyond the distal end of the outer tubular member; and a second extended position, wherein a second portion of the inner hollow needle member extends distally beyond the distal end of the outer tubular member, the second portion being longer than the first portion. Preferably, the spring member is more compressed in the second extended position than in the first extended position.

A stop member assembly, which limits extreme proximal motion of the inner tubular member and/or the stylet, also may be provided according to the present invention. In one embodiment, the inner tubular member comprises a biasing member biasing the inner tubular member into a contacting relationship with a second bearing surface to prevent retractable movement of the inner tubular member when in the retracted position. The stylet preferably includes a limiting surface, e.g., a kink, which acts to limit extreme proximal motion of the stylet when the limiting surface is biased against the distal end of the inner tubular member.

The invention may includes a rigid fixed tubular member having proximal and distal ends and coaxially received within the outer tubular member, wherein the proximal end of the fixed tubular member is attached to the leur lock mechanism, and wherein the fixed tubular member coaxially houses a portion of the inner tubular member and a portion of the stylet. A limiting member, which is fixed to the inner tubular member, may be provided, which biasly acts against the distal end of the fixed tubular member to prevent removal of the inner tubular member from the medical device. The stylet includes a kink which biasly acts against the distal end of the inner tubular member to prevent the removal of the stylet from the medical device.

BRIEF DESCRIPTION OF THE DRAWINGS

In the accompanying drawings which form a part of the specification and are to be read in conjunction therewith and in which like reference numerals are used to indicate like parts in the various views.

DETAILED DESCRIPTION OF THE INVENTION

Figure 1:
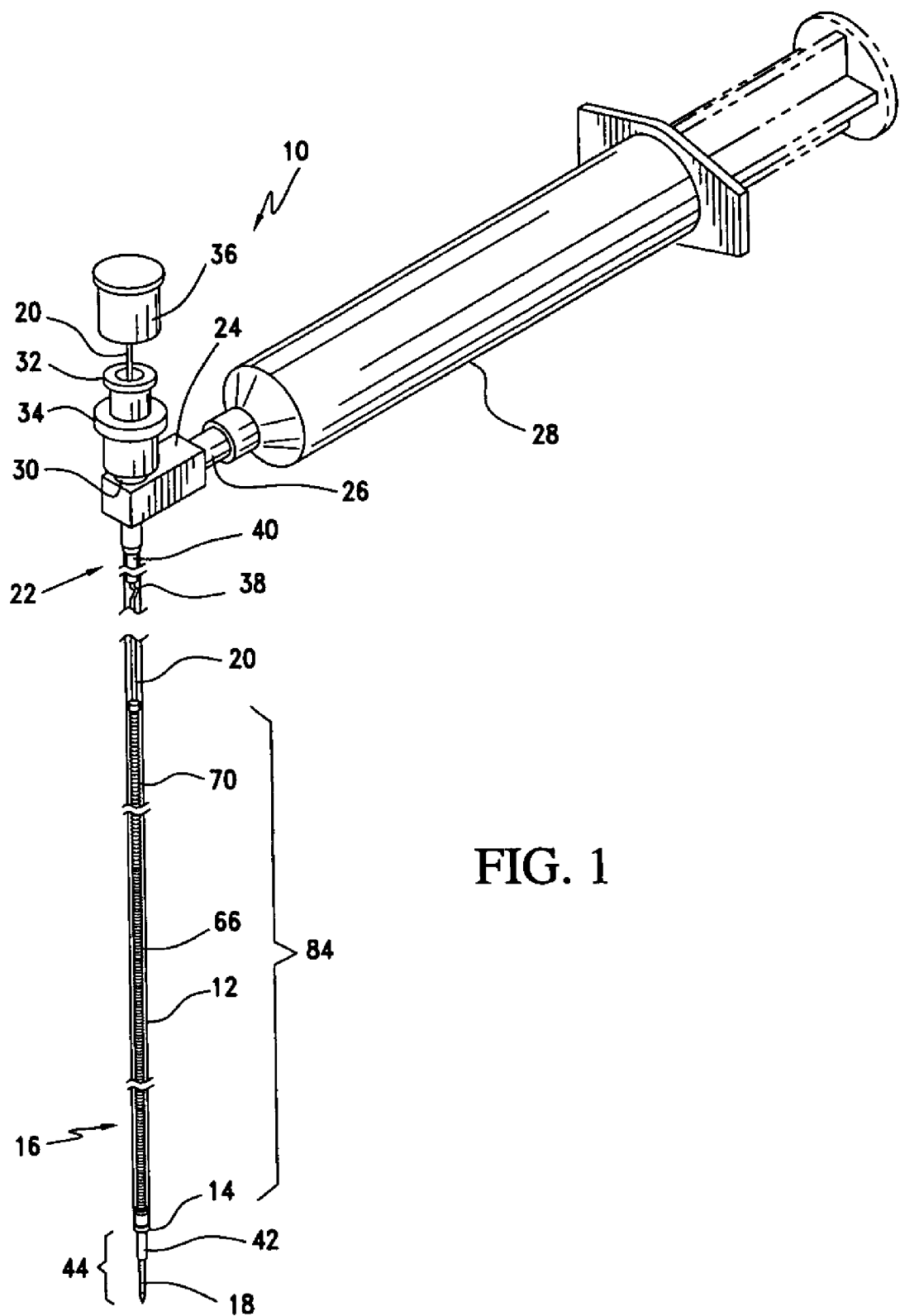
FIG. 1 is a representative perspective view of the biopsy needle assembly in accordance with one embodiment of the present invention.

The present invention is a medical device including a flexible outer tubular member, e.g., a flexible catheter, having proximal and distal ends. As used herein, the proximal end of a component of the medical device is the end of the component closest to the administering physician during normal use, and the distal end is the end of the component farthest away from the administering physician, e.g., the end closest to the target site, during normal operation. An inner tubular member having proximal and distal ends is slidably and coaxially received within the outer tubular member, and preferably is controllable by an administering physician operating a first grippable cap member. A flexible inner stylet, also having proximal and distal ends, is slidably and coaxially received within the inner tubular member and preferably is controllable by an administering physician with a second grippable cap member. A spring member, having proximal and distal ends, is oriented adjacent the distal end of the outer tubular member, the spring member being coaxially received within the outer tubular member and surrounding a portion of the inner stylet. The proximal end of the spring member is coupled to the stylet. A retractable outer hollow needle member having a proximal end is coupled to the distal end of the spring member. A retractable inner hollow needle member is slidably and coaxially received within the outer hollow needle member and includes a proximal end coupled to the distal end of the stylet.

In operation, the device has a retracted position wherein the inner and outer hollow needle members are completely housed within the outer tubular member. In this position the medical device is maneuverably movable through a patient's orifice to a target site. Once at the target site, the administering physician operates the first grippable cap member by moving the first grippable cap member in the distal direction and locking the first grippable cap member with a leur lock mechanism. By so doing, the medical device is provided in a first extended position wherein the outer hollow needle member and a first length of the inner hollow needle member, which includes the sharp point, extend beyond the distal end of the outer tubular member. The inner hollow needle member and, optionally, the outer hollow needle member penetrate the target site. The administering physician may then operate the second grippable cap member by moving the second grippable cap member in the distal direction and optionally locking the second grippable cap member with a second leur lock mechanism on the proximal end of the first grippable cap member. By moving the second grippable cap member in this fashion, the medical device forms a second extended position wherein the outer hollow needle member and a second length of the inner hollow needle member, which is longer than the first length, extend beyond the distal end of the outer tubular member. Optionally, the second grippable cap member is reciprocably and repeatedly operated in the proximal and distal directions thereby mechanically shearing the target lumen tissue into the cavity of the needle assembly and providing a desirable amount of tissue or cells for subsequent biopsy analysis.

FIG. 1 is representative of one embodiment of the present invention. As shown in FIG. 1, the medical device, generally designated 10, includes a flexible outer tubular member 12, e.g., a catheter, a metal tip 14 fixed to the distal end 16 of medical device 10 (preferably to the distal end of the outer tubular member 12), and a rigid hollow needle assembly 44, which includes an outer hollow needle member 42 and an inner hollow needle member 18 both of which are coaxial with tip 14 and outer tubular member 12. An inner tubular member 40, which preferably is rigid, is slidably received within outer tubular member 12. A flexible stylet 20 is slideably received within inner tubular member 40 for a purpose which will become clearer from the discussion below. The distal end 16 of the medical device 10 also preferably includes a spring member 84. Optionally, the spring member 84 includes a first spring section 66 normally having a first wavelength, and a second spring section 70 normally having a second wavelength, the second wavelength preferably being greater than the first wavelength while in an uncompressed state, e.g., while in the retracted position, and/or while in the first extended position. In another embodiment, not shown, the second wavelength is less than the first wavelength while in the retracted position, and/or while in the first extended position. The first and second spring sections may be integral with one another, or they may be formed of separate wire members that are attached together, e.g., by soldering, crimping, and/or with an adhesive or by other attachment means. The first and second spring sections are described in more detail with reference to FIGS. 2–4.

The proximal end 22 of the medical device 10 preferably includes a conventional two-directional leur lock 24, which includes one directional nipple 26 for accepting an aspirating device, e.g., a conventional syringe 28, and another directional nipple 30 being coaxially positioned relative to outer tubular member 12. An elastomeric seal, not shown, through which stylet 20 passes, is preferably provided on directional nipple 30 and/or on secondary directional nipple 32, discussed below. The elastomeric seal is provided to permit all suction forces generated by syringe 28 to be communicated through outer tubular member 12 and needle assembly 44 when it is desired to obtain biopsy tissue samples. Thus, no leakage will occur in the vicinity of stylet 20 where it passes through the elastomeric seal, yet reciprocal movement of stylet 20 through directional nipple 30 and secondary directional nipple 32 is permitted. Aspiration is effected through an annular space through which biopsy material can flow. The annular space is the region between the cavity of outer tubular member 12 and stylet 20.

A first grippable cap member 34 is fixed to a proximal end of the inner tubular member 40, which preferably is substantially rigid. Further, inner tubular member 40 preferably is slidably and coaxially received within the outer tubular member 12. The first grippable cap member 34 includes a threaded internal section, not shown, for providing a lockable relationship with directional nipple 30. FIG. 1 illustrates first grippable cap member 34 in a locked relationship with directional nipple 30.

A second grippable cap member 36 is fixed to the proximal end of stylet 20 so as to permit the attending physician to effect reciprocal movement thereof. Additionally or alternatively, a finger ring, not shown, may be provided on the first and/or second grippable cap members to allow the attending physician to extend and retract the needle assembly with a single hand. In one embodiment, not shown, a portion of the stylet may be adapted to pass through the first grippable cap member 34 and/or the second grippable cap member 36, and forms a circular shape thereby providing the finger ring. The proximal end of the first grippable cap member 34 includes a secondary directional nipple 32, which is adapted to have a lockable relationship with a threaded internal section, not shown, of the second grippable cap member 36. FIG. 1 illustrates second grippable cap member 36 in an unlocked relationship with secondary directional nipple 32.

Figure 2:
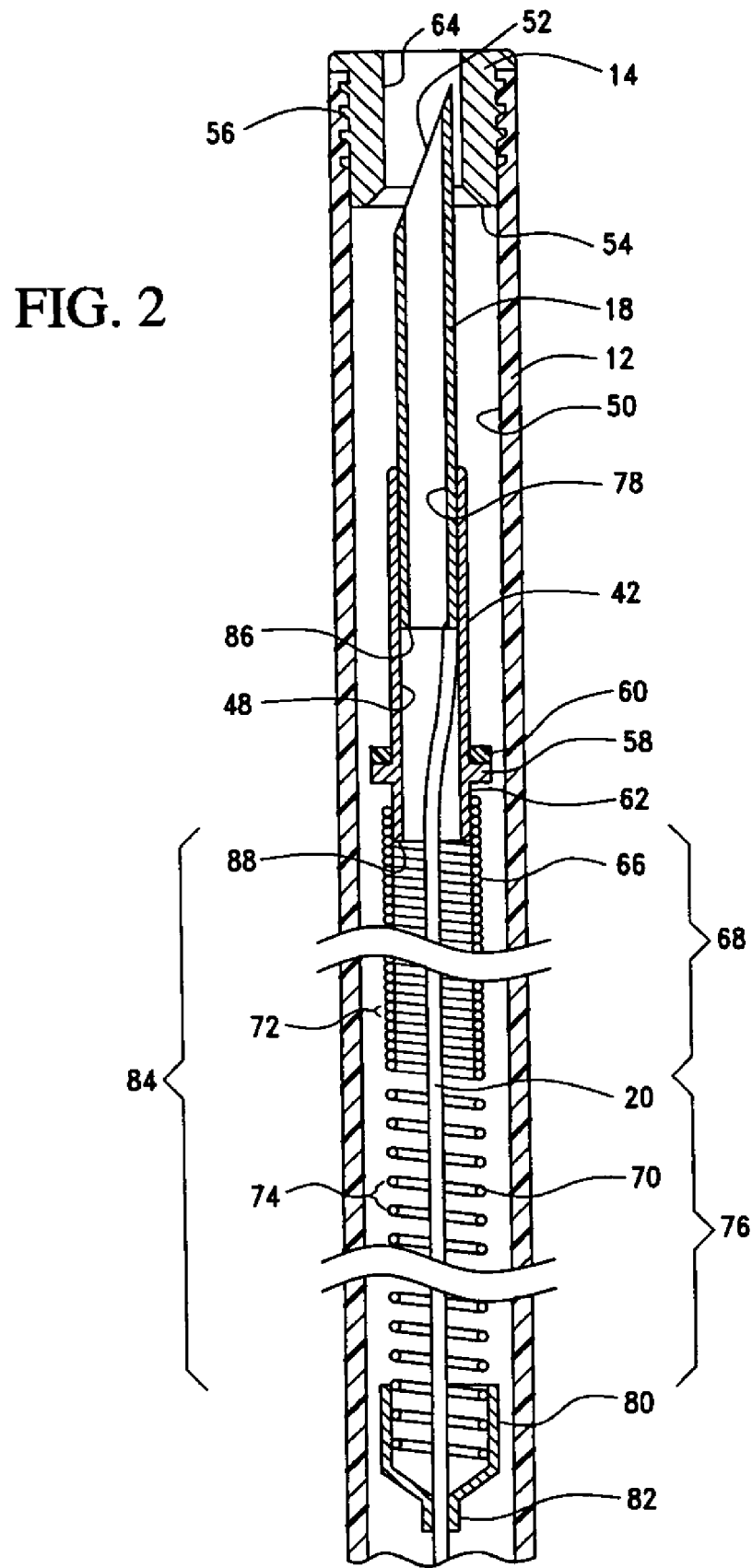
FIG. 2 is a detailed enlarged partial cross-sectional view of the distal end of the biopsy needle assembly of the present invention in the retracted position.

As illustrated in FIG. 2, in accordance with one embodiment of the present invention, the proximal end 88 of outer hollow needle member 42 is securely attached to a first spring 66 having proximal and distal ends. The first spring includes a plurality of turns of a wire member, each turn having a first wavelength 72, each wavelength being defined as the distance from one position on a first turn of the wire member to a similarly situation position on an adjacent turn of the wire member. The distal end of first spring 66 is preferably wrapped around and fixed to the proximal end 88 of outer hollow needle member 42. Preferably, the distal end of the first spring 66 is attached to the outer surface 62 of the proximal end 88 of outer hollow needle member 42 with an adhesive, solder, or mechanical means, e.g., crimping. Because the first spring 66 is fixedly secured around outer hollow needle member 42, the first spring is also preferably coaxially and slidably oriented within outer tubular member 12. Additionally or alternatively, a coupling member, not shown, may couple the distal end of the first spring 66 to the outer surface 62 of the outer hollow needle member 42 adjacent the proximal end 88 thereof. The coupling member may be a tubular member including a first end crimped over the needle and a second end crimped over the distal end of the first spring 66. Adhesive, solder or other mechanical means additionally or alternatively can be used to secure the coupling member to the outer needle member 42 and the first spring 66, thereby obtaining a secure union thereof. In another embodiment, not shown, the first spring 66 is attached to the inner surface 48 of outer hollow needle member 42 rather than the outer surface 62 thereof. In one embodiment, not shown, the proximal end of hub 58 may be adapted to receive the distal end of the first spring 66. In this embodiment, the hub 58, which may be secured to the first spring 66 by soldering, adhesive or mechanical means, e.g., crimping, acts as the coupling member.

The length of first spring 66 defines a first region of flexibility 68 as shown in FIG. 2. The first spring 66 provides for increased flexibility in the first region 68 of the medical device 10 of the present invention over conventional biopsy sampling devices. This increased flexibility provides significant advantages by allowing the distal end 16 of the medical device 10 to flexibly maneuver through a patient's orifice and to the target site to be sampled. Preferably, in the second extended position, illustrated in FIG. 4, the rigidity in the spring region between the proximal end 88 of outer hollow needle member 42 to the distal end of the coupling member 80 is relatively constant throughout because the first spring 66 and the second spring 70 are ideally fully compressed. However, in other embodiments, a slight deviation in rigidity may still exist between the first and second spring sections because of the inherent structural differences thereof.

The proximal end of first spring 66 is preferably coupled to or integral with a second spring 70 also having proximal and distal ends. The second spring 70 also includes a plurality of turns of a wire member, each turn defining a second wavelength 74, which, in one embodiment, is greater than the first wavelength 72 while the medical device 10 is in the retracted and first extended positions. Alternatively, the second wavelength 74 is less than the first wavelength 72 while the medical device 10 is in the retracted and first extended positions. Optionally, the distal end of second spring 70 is integral with or fixed to the proximal end of the first spring 66 with an adhesive, solder, a coupling member, e.g., a tubular member crimped or otherwise secured about the first and second springs, or by other mechanical means. As shown in FIG. 2, the first and second springs may be formed of a single wire member; that is, the first and second springs may be integral with one another. Second spring 70 is preferably oriented coaxially within outer tubular member 12. The length of second spring 70 defines a second region of flexibility 76 as shown in FIG. 2. The second spring 70 provides for increased flexibility in the second region 76 of the medical device of the present invention over conventional biopsy sampling devices. Moreover, the mechanical properties of second spring 70 are preferably such that the flexibility within the second region 76 is different from (either greater than or less than) the flexibility in the first region 68 while the needle is in the retracted position. This increased flexibility provides significant advantages by allowing the distal end 16 of the medical device 10 to flexibly maneuver through a patient's orifice and to the target site to be sampled.

As shown in FIG. 2, stylet 20 is preferably oriented coaxially within first spring 66 and second spring 70 and extends entirely therethrough whether the needle assembly 44 is retracted or extended. The proximal end of second spring 70 is preferably fixedly attached to the stylet 20 with a coupling member 80. Coupling member 80, in one embodiment, is a substantially rigid sheath or tubular member formed ideally of a metal or a metal alloy, e.g., stainless steel. The coupling member 80 surrounds the proximal end of second spring 70 and is secured thereto, e.g., with an adhesive, solder, or by mechanical means such as crimping. The coupling member is also fixedly secured to the stylet 20 at the proximal end 82 of the coupling member 80, preferably by solder, adhesive, crimping or other mechanical means.

The needle assembly 44 of the present invention is particularly well suited for use in combination with a flexible fiberoptic bronchoscope, which should be flexible. As used herein and in the appended claims, the term "flexible" is meant to refer to axial flexion through an arc of 360 degrees, e.g., axially looped. Such flexibility permits the needle assembly to negotiate sharp turns even to the extent of permitting U-turns thereof.

In order to permit such flexibility, outer tubular member 12 is preferably constructed of a durable plastic material. Similarly, stylet 20 can be constructed of fine gauge metal or plastic wire, the flexibility thereof being substantially equal to the flexibility of the outer tubular member 12 in which it is slideably received.

Figure 3:
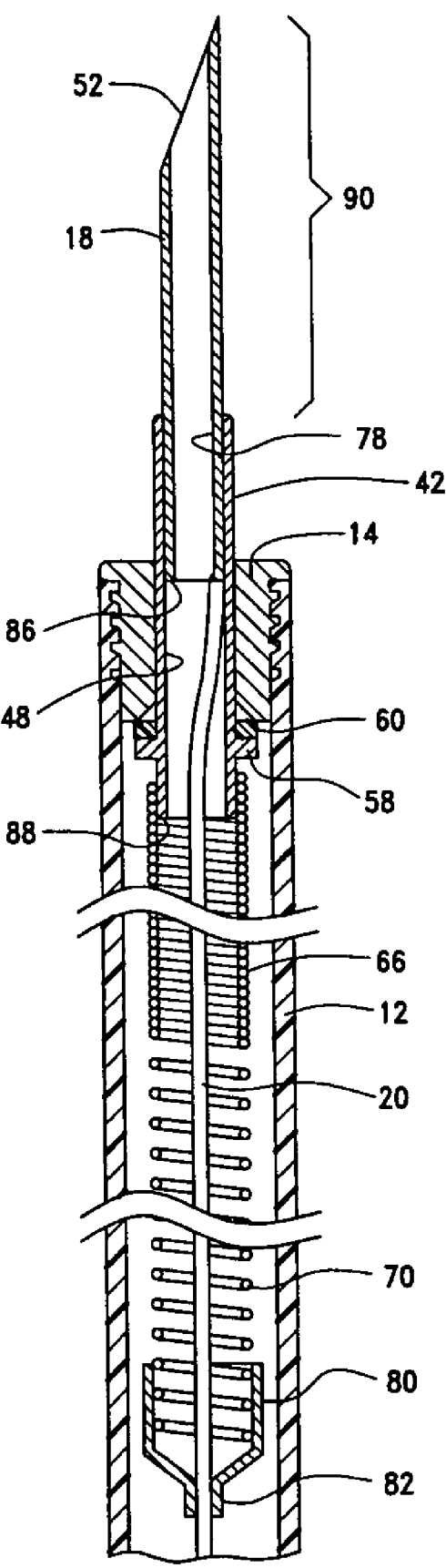
FIG. 3 is a detailed enlarged partial cross-sectional view of the distal end of the biopsy needle assembly of the present invention in a first extended position.
Figure 4:
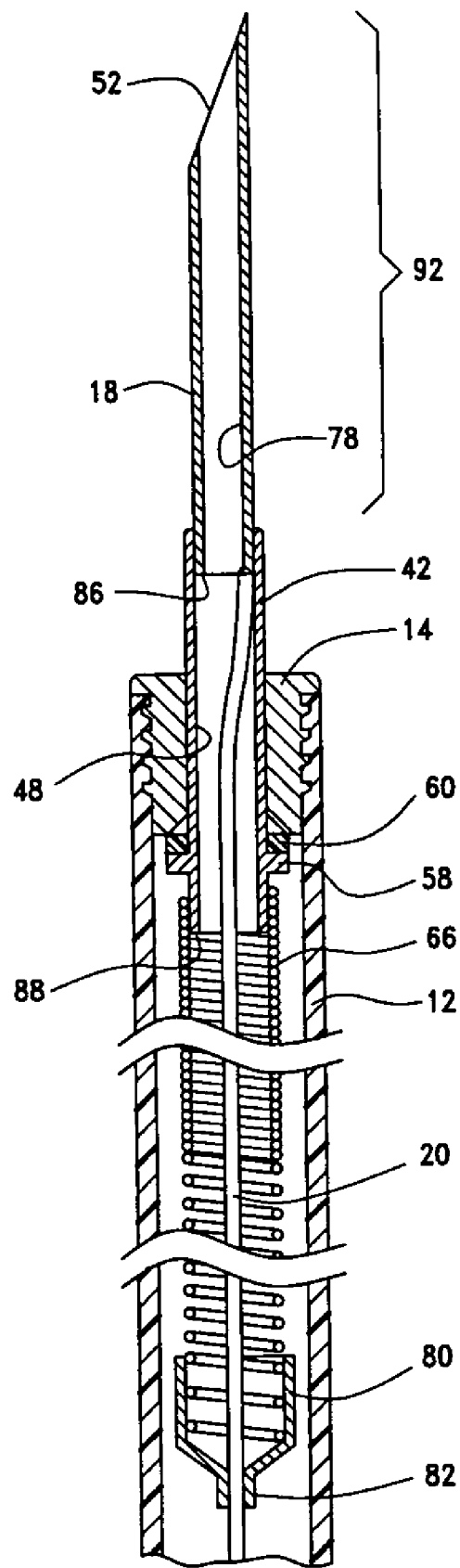
FIG. 4 is a detailed enlarged partial cross-sectional view of the distal end of the biopsy needle assembly of the present invention in a second extended position.

FIG. 2 illustrates needle assembly 44 in a retracted position in accordance with one embodiment of the present invention. As shown, the needle assembly 44, which includes outer hollow needle member 42 and inner hollow needle member 18, is in a retracted position with the entire needle assembly 44 housed within outer tubular member 12. Because the inner hollow needle member 18 is housed at least partially within the outer hollow needle member 42 while in the retracted position, the distal end of the medical device can be easily maneuvered in a serpentine manner through a patient's orifice to the target site. In the retracted embodiment shown in FIG. 2, the first grippable cap member 34 and the second grippable cap member 36, not shown in FIGS. 2–4, are in unlocked positions and extended to the extent necessary in the proximal direction in order to maintain the needle assembly 44 in a retracted state.

The inner hollow needle member 18 is reciprocably movable within outer hollow needle member 42. Preferably, stylet 20 is attached to the proximal end 86 of the inner hollow needle member 18. The stylet 20 can be attached to the inner hollow needle member 18 by a variety of means, e.g., an adhesive, solder, or by mechanical means, e.g., crimping, or other attaching means. The needle assembly 44 is reciprocally movable within outer tubular member 12 and tip 14 as stylet 20 is moved in the proximal and distal directions.

The inner surface 48 of the outer hollow needle member 42 and the inner surface 78 of the inner hollow needle member 18 define a needle cavity for receiving a tissue sample from a patient's target site. The needle cavity preferably is substantially cylindrical throughout its entire length although the flexibility of the device can provide for deviations from a cylindrical form. In one embodiment, the needle cavity is coaxially situated within an interior cavity formed by the inner surface 50 of the outer tubular member 12, the diameter of the former being preferably about one-third to about one-half that of the latter. Stylet 20, on the other hand, optionally is sized so as to be closely received within the needle cavity. Thus, stylet 20 preferably is similarly about one-third to about one-half the diameter of interior cavity of the needle assembly so as to establish a significant annular space through which biopsy tissue and/or fluids can easily flow.

The distal end of the inner hollow needle member 18 defines a sharp edge 52 for penetrating a patient's tissue while in an extended position (see FIGS. 3 and 4) to obtain samples thereof, while the proximal end 86 of the inner hollow needle member 18 is attached to the distal end of the stylet 20, as discussed above. The distal end of the outer hollow needle member 42 slidably receives at least a portion of the inner hollow needle member 18. In another embodiment, not shown, the distal end of the outer hollow needle member 42 also defines a sharp edge for facilitating penetration into a patient's tissue when in an extended position. The proximal end 88 of the outer hollow needle member 42 preferably is attached to first spring section 66, as described above. It should be understood that while the tip of the inner hollow needle member 18 has been shown as being pointed and sharpened in a conventional way, the inner hollow needle member 18 could have any shape that would accomplish the desired purpose of collecting tissue specimens. Alternatively, for example, a brush may be implemented in the present invention in lieu of a needle, as described by U.S. Pat. No. 4,966,162 to Wang, the entirety of which is incorporated herein by reference.

Outer hollow needle member 42 also includes a fixed hub 58 which preferably encircles the outer hollow needle member 42 adjacent the proximal end thereof. The hub 58 may be attached to the needle with an adhesive, solder, or by mechanical means, e.g., crimping, or the hub 58 may be integral with the outer hollow needle member 42, as shown in FIGS. 2–4. The hub 58 includes a distally-facing surface which acts as a limit member to limit extreme distal movement of outer hollow needle member 42. The limiting function of hub 58 is achieved by ensuring that the distally-facing surface of hub 58 bears against a bearing member such as proximal end 54 of tip 14. Thus, hub 58 preferably is also constructed of a hard material, such as stainless steel or the like.

In one particularly preferred embodiment, not shown, the hub 58 is formed by crimping a portion of the outer hollow needle member 42, preferably in a region adjacent the proximal end thereof. In this embodiment, the crimped region of the outer hollow needle member has a region of increased width, which is wider than the opening formed by the proximal end of tip 14. The region of increased width formed by the crimping acts as a limiting member against proximal end 54 of tip 14, thereby ensuring that the outer hollow needle member 42 cannot extend beyond the distal end of tip 14. This embodiment may provide the additional advantage of providing a securing means for attaching the first spring 66 to the outer hollow needle member 42. For example, the distal end of first spring 66 may extend inside the proximal end of outer hollow needle member 42 and may be secured to the outer hollow needle member 42 by crimping the outer surface 62 thereof.

Optionally, a pliable O-ring 60 is fixedly or removably oriented against the distally-facing surface of hub 58. When the needle assembly is in an extended position, the O-ring provides a seal with proximal end 54 of tip 14. This seal advantageously reduces or eliminates annular flow between outer surface 62 of outer hollow needle member 42 and inner surface 64 of metal tip 14. Thus, as suction is created by the aspirating device, a pressure drop is created within outer tubular member 12 and the needle cavity within the needle assembly thereby facilitating biopsy tissue and/or fluid flow into the needle cavity. Optionally, the fluid or biopsy tissue flows through the needle assembly and into the inner cavity defined by the first spring 66. The fluid or biopsy tissue also may flow into the inner cavity defined by the second spring 70 and the outer tubular member 12.

Once the medical device has been maneuvered through a patient's orifice to a patient's target site, the administering physician may apply a pressure in the distal direction on the first grippable cap member 34. The physician optionally may lock the first grippable cap member 34 to the leur lock 24 by turning the first grippable cap member 34 about its axis while applying pressure in the distal direction. By so doing, the threaded internal section, not shown, of the first grippable cap member 34 may be lockingly engaged with directional nipple 30 of leur lock 24. As the first grippable cap member 34 is moved in the distal direction, the inner tubular member 40, the proximal end of which is coupled to the first grippable cap member 34, also moves in the distal direction. As indicated above, stylet 20 is reciprocably and coaxially received within inner tubular member 40. Preferably, the stylet 20 includes a kink 38 (see FIG. 5) or other limiting member, which is provided to provide a biasing force against the distal end of the inner tubular member 40. Preferably, the kink 38 is positioned on the stylet 20 such that the distance that the second grippable cap member 36 is movable in the proximal direction is limited thereby ensuring that the inner hollow needle member 18 may not be withdrawn from the needle assembly, e.g., into the spring member 84. Thus, the kink 38 limits the distance that the second grippable cap member 36 may be moved in the proximal direction relative to the first grippable cap member 34, because the kink will ultimately be biased against the distal end of the inner tubular member 40. In an alternate embodiment, the stylet 20 may be provided with a different type of limiting member such as a cylindrical member, not shown, which can be securely attached to the stylet 20, e.g., by crimping, adhesive, or other attachment means.

The kink 38 provides the additional advantage of transferring energy to the stylet 20 as the inner tubular member 40 is moved in the distal direction. While in the retracted position as in FIG. 2, both the first and second grippable cap members are in unlocked positions and are positioned proximally from the leur lock 24. As the first grippable cap member 34 is moved in the distal direction, the distal end of the inner tubular member 40 moves and contacts the kink 38 in stylet 20 so that further axial movement of inner tubular member 40 moves stylet 20 thereby causing the stylet 20 and the second grippable cap member 36 to also move in the distal direction. As the stylet 20 moves in the distal direction, energy is transferred to the inner hollow needle member 18, the proximal end 86 of which is attached to the distal end of the stylet 20. Additionally, energy is transferred to coupling member 80, which is attached to the stylet 20, and to the spring member 84, which is attached to the coupling member 80. Thus, the entire needle assembly and spring mechanism, preferably with minimal compression thereof, is moved distally as the second grippable cap member is moved in the distal direction. After the first grippable cap member 34 has been fully moved in the distal direction, and optionally locked to directional nipple 30, the medical device will be changed to the first extended position, as illustrated in FIG. 3.

In the first extended position, at least a portion of the needle assembly 44 is extended beyond the distally facing surface of tip 14. Preferably, at least a portion of the outer hollow needle member 42 and a first length 90 of the inner hollow needle member 18 extend distally beyond the tip 14 of the outer tubular member 12. As the administering physician extends the needle assembly 44 distally beyond tip 14 of the outer tubular member 12, at least a portion of the inner hollow needle member 18 and, optionally, a portion of the outer hollow needle member 42 penetrates the target site. The length of inner tubular member 40 preferably provides that as the first grippable cap member 34 is fully extended in the distal direction and optionally locked with directional nipple 30, the distally facing surface of hub 58 (or distally facing surface of optional O-ring 60) contacts proximal end 54 of tip 14. Minor compression of the first and/or second spring sections may also occur as the needle assembly 44 is extended to the first extended position. After the first grippable cap member 34 has been fully advanced in the distal direction, the first grippable cap member 34 preferably is lockingly engaged with directional nipple 30 on leur lock 24, as discussed above.

Figure 8:
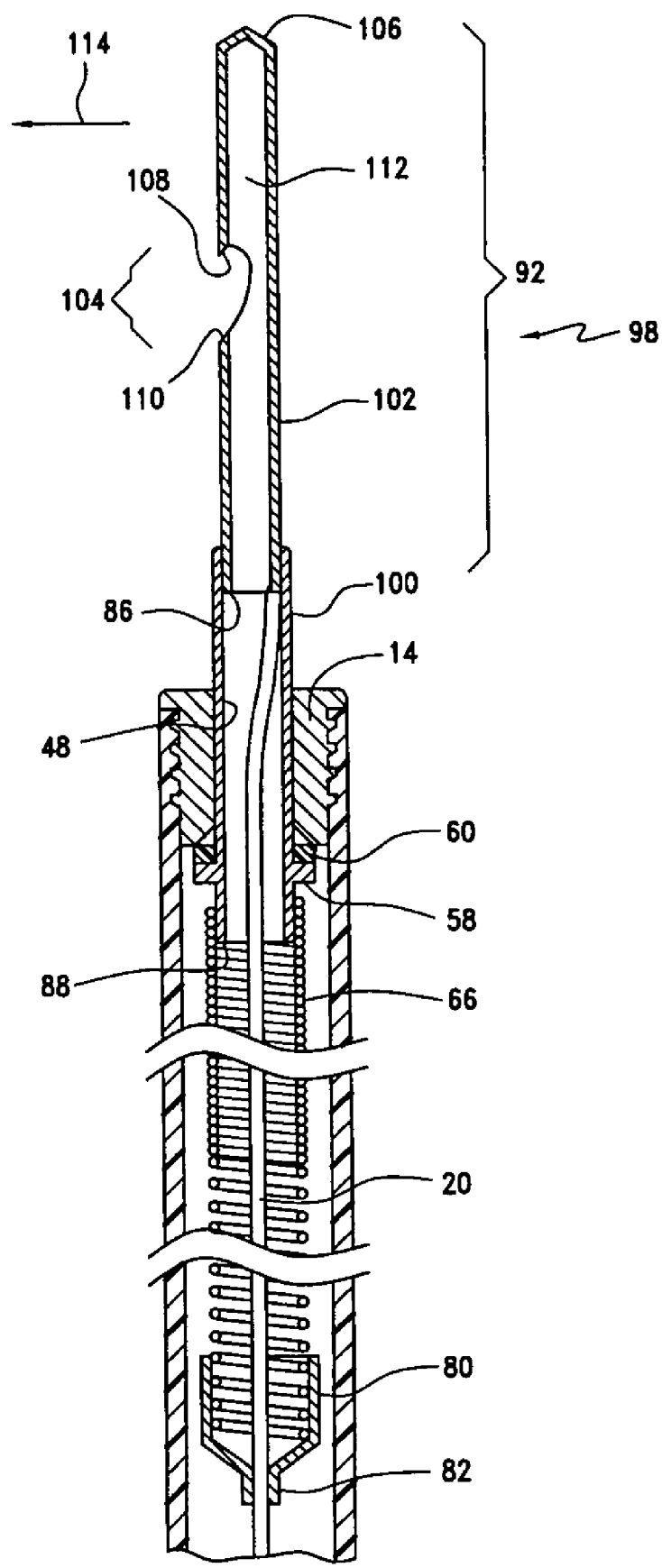
FIG. 8 is a detailed partial cross-sectional view of the distal end of the histology inner cut needle embodiment of the present invention in a second extended position.

FIG. 4 illustrates a medical device according to the present invention, wherein the needle assembly is in a second extended position in which the inner hollow needle member 18 is extended a second length 92. The second length 92 of the second extended position is longer than the first length 90 of the first extended position. After locking the first grippable cap member 34 onto directional nipple 30 on leur lock 24 and thereby establishing the first extended position, the administering physician may apply pressure in the distal direction on the second grippable cap member 36 to further extend the inner hollow needle member 18 to the second extended position. The proximal end of the stylet 20 is coupled to the second grippable cap member 36. Accordingly, as the second grippable cap member 36 is moved in the distal direction, the stylet 20 also moves in the distal direction. The distal end of the stylet 20 is attached to the proximal end of the inner hollow needle member 18, as described above. Thus, as the second grippable cap member 36 is moved in the distal direction, the inner hollow needle member 18 is further extended in the distal direction. Additionally, a biasing force is created between the proximal end 54 of tip 14 and the hub 58 (or the optional O-ring 60), thereby causing the spring member 84 (including the first and/or second spring sections) to compress as the medical device progresses from the first extended position to the second extended position. For purposes of clarity, FIGS. 4 and 8 illustrate the second spring section 70 in a partially compressed state. Preferably, however, upon extension of the device to the second extended position, the second spring section 70 is fully compressed and may have a wavelength that is the same as first spring section 66. The physician optionally may lock the second grippable cap member 36 to the secondary nipple 32 on first grippable cap member 34 by turning the second grippable cap member 36 about its axis while applying pressure in the distal direction. By so doing, the threaded internal section, not shown, of the second grippable cap member 36 may be lockingly engaged with secondary directional nipple 32 on first grippable cap member 34. If desired, the administering physician may repeatedly move the second grippable cap member 36 reciprocally between the first and second extended positions. By operating the device in this manner, the needle can shear tissue from a patient's target site, and the physician may apply a suction with the aspirating device to obtain a desirable biopsy sample.

Thus, when stylet 20 is locked in the second extended position with the interaction between second grippable cap member 36 and secondary nipple 32, compressed second spring 70 applies a constant biasing force which is transferred through first spring 66 and needle assembly 44. In this manner, a biasing force of sufficient magnitude will be exerted against needle assembly 44 to ensure that hub 58 or O-ring 60 bears against proximal end 54 of tip 14 thereby establishing rigid extension of needle assembly 44 to prevent undesired retraction thereof.

This locking feature of the present invention ensures that the biasing force on needle assembly 44 is provided so as to resist compression forces tending to retract needle assembly 44 into outer tubular member 12. Resisting compression forces is extremely important when consideration is given to the fact that oftentimes relatively tough tissue must be penetrated (e.g. bronchial walls or hard tumors) in order to obtain the desired biopsy material. Thus, such tough tissue may exert a sufficient amount of resistance against needle assembly 44 so as to cause at least partial retraction thereof into outer tubular member 12. Such unintended partial retraction of needle 18 is to be strictly avoided. For example, should partial retraction occur, the attending physician would not be able to completely penetrate the bronchial wall in order to obtain a biopsy sample of the lymph nodes therebehind. This inability may lead to a misdiagnosis of the patient's ailment, for example, as the tissue sample which will be obtained will not be of the diseased lymph node, but rather will be of the undiseased bronchial wall.

After the needle assembly 44 has satisfactorily penetrated the target site and after the physician has optionally sheared the tissue from the target site, the second grippable cap member 36 preferably is unlocked from secondary directional nipple 32 and the needle assembly 44 is placed in the first extended position by allowing the second spring 70 to uncompress and/or optionally by moving the second grippable cap member 36 in the proximal direction. While in this uncompressed state, gaps are provided between adjacent bends of the wire member defining the second wavelength 74 of second spring 70. A suction is then desirably provided by the aspirating device thereby causing fluid or biopsy tissue to flow through the needle assembly 44 and first spring 66 and into second spring 70. The fluid or tissue then flows through the spaces or gaps between adjacent turns of the wire forming the second spring 70 and into the interior cavity of the medical device. After the biopsy tissue or fluid has been sampled, the medical device is placed in the retracted position and removed from the patient's body. The tissue or fluid can then be analyzed in order to diagnose the patient's ailment. If desired, suction may be applied while the medical device 10 is in the second extended position.

The length of the inner and outer hollow needle members may vary widely in accordance with the present invention depending factors such as the depth of the biopsy sought and the patient's illness. As used herein, the length of the outer hollow needle member 42 is the length from the extreme distal end thereof to the distally facing surface of hub 58; the length of the inner hollow needle member 18 is the length from the extreme distal end thereof to the extreme proximal end thereof. In one embodiment, the length of the outer hollow needle member 42 is greater than about 0.5 cm, more preferably greater than about 0.6 cm, and most preferably greater than about 0.7 cm. In terms of upper range limits, the length of outer hollow needle member 42 preferably is less than about 1.3 cm, more preferably less than about 1.1 cm, and most preferably less than about 0.9 cm. The length of the inner hollow needle member 18 preferably is greater than about 0.5 cm, more preferably greater than about 0.6 cm, and most preferably greater than about 0.8 cm. In terms of lower range limits, the length of inner hollow needle member 18 preferably is less than about 1.3 cm, more preferably less than about 1.1 cm, and most preferably less than about 0.9 cm. The overall length of the needle assembly 44 in the first extended position, measured from the distally facing surface of hub 58 to the extreme distal end of inner hollow needle member 18, preferably is from about 0.6 cm to about 1.4 cm, more preferably from about 0.8 cm to about 1.2 cm, and most preferably from about 0.9 cm to about 1.1 cm. The overall length of the needle assembly 44 in the second extended position, measured from the distally facing surface of hub 58 to the extreme distal end of inner hollow needle member 18, preferably is from about 1.3 cm to about 2.0 cm, more preferably from about 1.5 cm to about 2.0 cm, and most preferably from about 1.5 cm to about 1.8 cm. One advantage of the present invention is that the overall length of the needle assembly 44 in the first extended position can be significantly shorter than conventional biopsy needles, thereby facilitating perpendicular entry into a target site. Also, the overall length of the needle assembly 44 in the second extended position can be significantly longer than conventional biopsy needles, thereby ensuring that the needle assembly 44 can penetrate the target site at sufficient depth to obtain a satisfactory biopsy.

The diameters of the inner and outer hollow needle members also may vary widely according to the present invention. Preferably, the outer hollow needle member 42 has a diameter of from about 17 to about 21 gauge, more preferably from about 18 to about 20 gauge, and most preferably about 19 gauge. The inner hollow needle member 18 preferably has a diameter of from about 19 to about 23 gauge, more preferably from about 20 to about 22 gauge, and most preferably about 21 gauge.

Tip 14 is an important feature of the present invention in that it effects secure union between needle assembly 44 and outer tubular member 12 thereby preventing deleterious separation thereof. Tip 14 is preferably constructed of a hard metal, e.g., stainless steel, or a hard plastic material. In accordance with the embodiment of FIG. 2, tip 14 is provided with a male threaded member 56 so that when threadingly inserted into the interior cavity of the outer tubular member 12, the male threaded member 56 acts as a tapping tool to cut corresponding female threads into outer tubular member 12. Thus, a self-tapping system is established whereby axial forces will be resisted thereby preventing separation of tip 14 and needle assembly 44 from outer tubular member 12.

By implementing the second spring 70 in accordance with the present invention, the desired rigidity of the device when taking samples is not decreased. In the retracted and first extended positions, illustrated in FIGS. 2 and 3, respectively, the second spring is in an uncompressed (or slightly compressed) and highly flexible state desirous for maneuvering the device through the patient's orifice. The overall flexibility of a medical device 10 including the spring member 84 and an internal stylet 20 will be much more flexible and thus more easily positioned within the patient than conventional devices. Surprisingly, when the second spring 70 is in the second extended position, illustrated in FIG. 4, under compression and fully loaded with a limiting member such as the distally-facing surface of hub 58 or optional O-ring 60 in contact with proximal end 54 of tip 14, the needle assembly 44 will be under rigid conditions able to withstand the repeated penetrations into tissue that are desirable in order to obtain the sampling.

Figure 5:
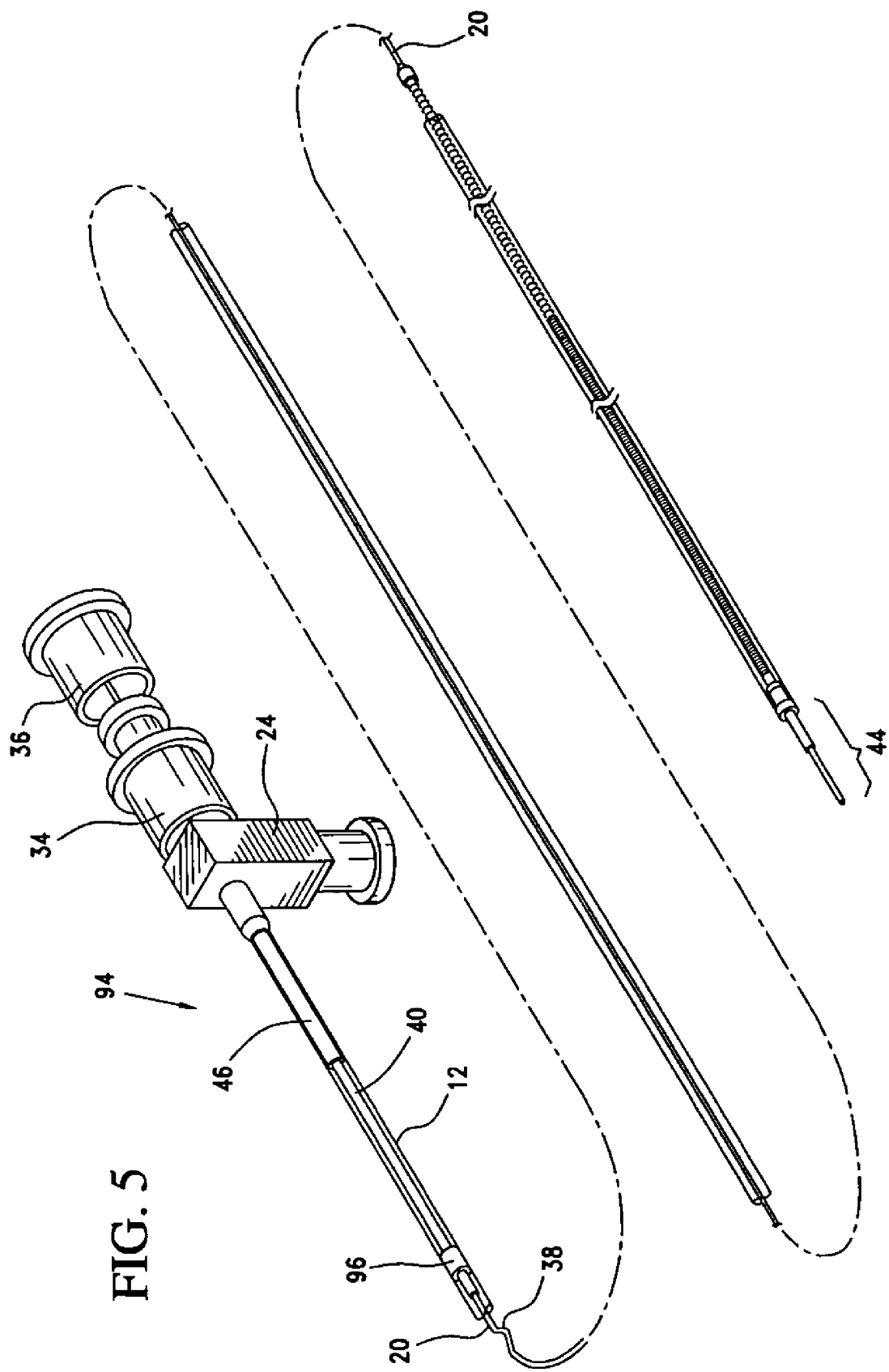
FIG. 5 is a perspective view of one embodiment of the present invention showing the stop member assembly.

FIG. 5 illustrates another embodiment of the medical device 10 showing a stop member assembly, generally designated 94, which desirably prevents separation of the inner tubular member 40 from the outer tubular member 12 and also provides a guide for the administering physician that the needle assembly 44 is in a fully retracted position. As shown in FIG. 5, in one embodiment, leur lock 24 is attached at its distal end to a fixed tubular member 46, which has proximal and distal ends. Fixed tubular member 46 is a rigid tubular member, which is secured to the leur lock 24, e.g., by an adhesive such as glue, crimping, soldering, or other attachment means. The fixed tubular member 46 is coaxially oriented within a proximal portion of outer tubular member 12. Inner tubular member 40 is slidably and coaxially received within the fixed tubular member 46 and, in one embodiment, includes a limiting member 96 which is adapted to act as a biasing member against the distal end of fixed tubular member 46. In the embodiment shown in FIG. 5, the limiting member 96 is an external sleeve formed of a rigid material and is secured to the inner tubular member 40 by crimping, adhesive, soldering or other attachment means. Preferably, the width or diameter of the outer sleeve is wider than the width or diameter of the distal end of fixed tubular member 46. Accordingly, the stop member assembly 94 provides an extreme limit of proximal motion for the first grippable cap member 34 and the inner tubular member 40, which is attached thereto. Further, the stop member assembly 94 provides an extreme limit of proximal motion for the second grippable cap member 36 and stylet 20, which is attached thereto, because the kink 38 in stylet 20 acts as a limiting member against the distal end of the inner tubular member 40, as discussed above.

In another embodiment, not shown, an external ring member having a first diameter is fixed, e.g., crimped, about the outer tubular member 12 between the distal end of leur lock 24 and the limiting member 96, which is wrapped about the inner tubular member 40. The external ring member provides a region of reduced diameter in outer tubular member 12. The region of reduced diameter preferably has a width or diameter that is less than the diameter of the limiting member 96. As the inner tubular member 40 is moved in the proximal direction, the limiting member 96 provides an extreme limit of proximal motion for the inner tubular member 40 as the limiting member 96 is biased against the region of reduced diameter in the outer tubular member 12. In this embodiment, no fixed tubular member 46 is required.

Figure 6:
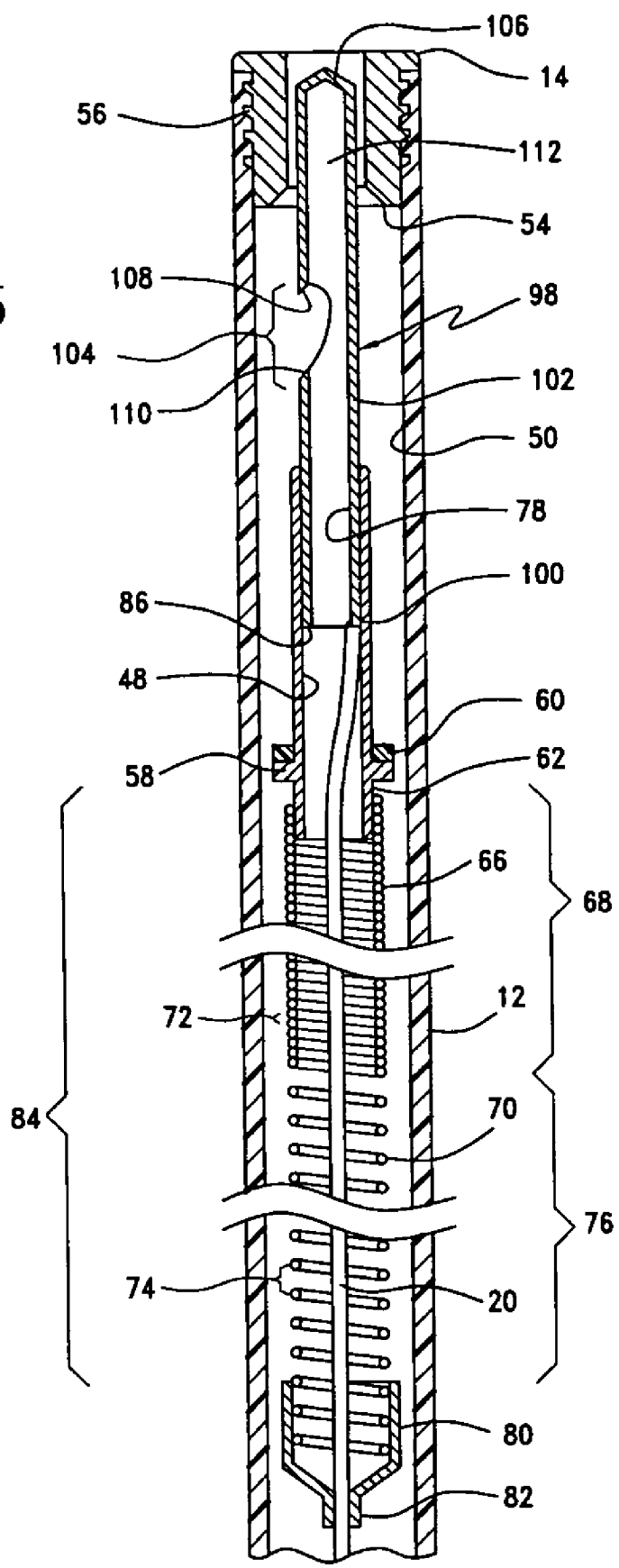
FIG. 6 is a detailed partial cross-sectional view of the distal end of a histology inner cut needle embodiment of the present invention in the retracted position.
Figure 7:
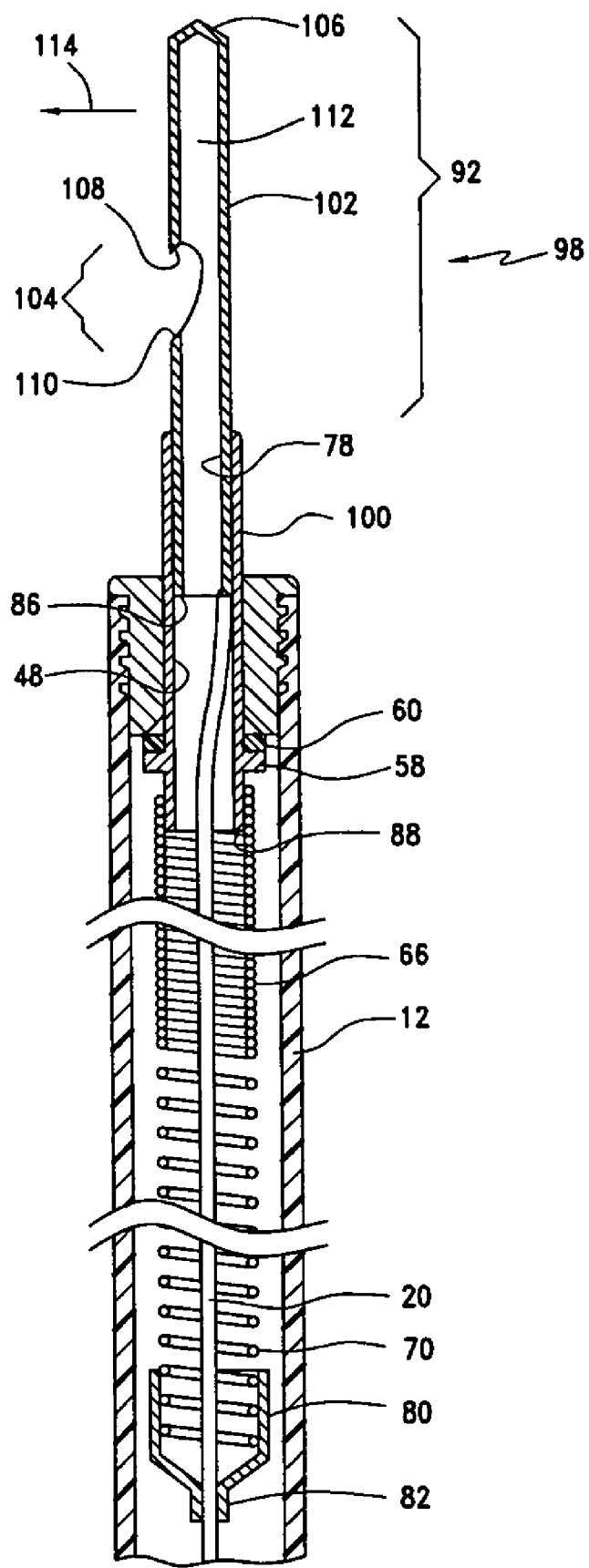
FIG. 7 is a detailed partial cross-sectional view of the distal end of the histology inner cut needle embodiment of the present invention in a first extended position.

FIGS. 6–8 illustrate another particularly desirable embodiment of the present invention wherein the needle assembly includes a histology inner cut needle assembly, generally designated 98. The histology inner cut needle assembly 98 includes an outer hollow needle member 100, which operates identically to outer hollow needle member 42 of the embodiment illustrated in FIGS. 1–5. The histology inner cut needle assembly 98 also includes an inner needle member 102 having proximal and distal ends and a side gap 104. Unlike conventional needles, the distal end 106 of inner needle member 102 preferably is closed off. The side gap 104 preferably includes a trocar shaped edge 108 on the distal end of the side gap 104 and a rounded edge 110 on the proximal end of the side gap 104. In operation, the histology inner cut needle assembly 98 operates in a manner similar to the embodiment disclosed with reference to FIGS. 1–5. That is, the needle assembly includes three positions: a retracted position, which is illustrated in FIG. 6; a first extended position, which is illustrated in FIG. 7; and a second extended position, which is illustrated in FIG. 8. Unlike the previous embodiment, however, the side gap 104 acts to collect a tissue or biopsy sample by moving in the proximal direction. As the inner needle member 102 moves in the proximal direction, a lateral force, illustrated by arrow 114 in FIG. 8, preferably is exerted in the radial direction of the side gap. Preferably, the second cap member has an indication thereon which indicates the required direction for the lateral force. The trocar edge 108 of side gap 104 acts to shear or tear away tissue from the target site as the inner tubular member 102 is moved in the proximal direction. Preferably, the administering physician operates the needle assembly in a reciprocal manner between the first and second extended positions, as with the previous embodiment, and tissue is received in the containment area 112, which preferably is oriented distally to the side gap 104. Suction may be created by an aspiration device, not shown, to facilitate sampling of the target site. After obtaining the tissue or biopsy sample, the needle assembly is retracted into the outer tubular member and safely withdrawn from the patient's orifice.

In the embodiment shown in FIGS. 6–8, the outer hollow needle member 100 preferably has a diameter of from about 15 to about 19 gauge, more preferably from about 16 to about 18 gauge, and most preferably about 17 gauge. The inner hollow needle member 102 preferably has a diameter of from about 17 to about 21 gauge, more preferably from about 18 to about 20 gauge, and most preferably about 19 gauge. The outer hollow needle member 110 preferably has a length, measured from the hub thereof to the distal end thereof, of from about 0.5 cm to about 10.5 cm, more preferably from about 0.7 cm to about 1.3 cm, and most preferably from about 0.9 to about 1.1 cm. The inner hollow needle member 102 preferably has a length, measured from the proximal end thereof to the distal end thereof, of from about 0.5 cm to about 1.5 cm, more preferably from about 0.7 cm to about 1.3 cm, and most preferably from about 0.9 to about 1.1 cm. The length of the side gap preferably is from about 0.3 cm to about 0.7 cm, and more preferably from about 0.4 to about 0.6 cm.

While the invention has been described in connection with what is presently considered to be the most practical and preferred embodiment, it is to be understood that the present invention is not limited to the disclosed embodiment, but, to the contrary, it is intended to cover various modifications and equivalent arrangements included within the spirit and scope of the appended claims.

I claim:

1. A medical device, comprising:
   a flexible outer tubular member having proximal and distal ends;
   a flexible inner stylet having proximal and distal ends slidably and coaxially received within the outer tubular member;
   a spring member having proximal and distal ends oriented adjacent the distal end of the outer tubular member, the spring member being coaxially received within the outer tubular member and surrounding a portion of the inner stylet, wherein the proximal end of the spring member is coupled to the stylet;
   a retractable outer hollow needle member having a proximal end coupled to the distal end of the spring member; and
   a retractable inner hollow needle member slidably and coaxially received within the outer hollow needle member and having a proximal end coupled to the distal end of the stylet;
   wherein the device has a retracted position wherein the inner and outer hollow needle members are completely housed within the outer tubular member, a first extended position wherein the outer hollow needle member and a first length of the inner hollow needle member extend beyond the distal end of the outer tubular member, and a second extended position wherein the outer hollow needle member and a second length of the inner hollow needle member extend beyond the distal end of the outer tubular member, the second length being longer than the first length.

2. The device of claim 1, wherein the spring member is more compressed in the second extended position than in the first extended position.

3. The device of claim 1, further comprising:
   a bard tip rigidly fixed to the distal end of the outer tubular member, the tip, including a bearing surface on the proximal end thereof.

4. The device of claim 3, wherein the outer hollow needle member comprises a limiting member rigidly associated with the outer hollow needle member and contacting the bearing surface of the tip member in the first and second extended positions.

5. The device of claim 1, wherein the spring member comprises first and second portions, the first portion is oriented distally with respect to the second portion, and wherein the distal end of the first portion is attached to the outer hollow needle member and the proximal end of the second portion is attached to the stylet.

6. The device of claim 5, wherein the second portion is uncompressed in the first extended position.

7. The device of claim 6, wherein the second portion is partially compressed in the second extended position.

8. The device of claim 1, further including an inner tubular member attached to a first grippable cap member, and the stylet is attached to a second grippable cap member.

9. The device of claim 1, wherein the inner hollow needle meinber comprises a side gap which includes trocar edge.

10. A tissue collection device, comprising:
    an elongated outer flexible hollow catheter having proximal and distal ends;
    an elongated stylet slidably positioned within the hollow cather;
    a helically wound wire member having proximal and distal ends and having a portion thereof coaxially attached to the stylet;
    an outer hollow needle member attached to the distal end of the helically wound wire member; and
    an inner hollow needle member telescopically received within the outer hollow needle member and attached to a distal portion of the stylet the inner hollow needle member including a sampling portion.

11. The device of claim 10, wherein the sampling portion comprises a sharp edge on the distal end of the inner hollow needle member.

12. The device of claim 10, wherein the sampling portion is a side gap having a sharp trocar edge.

13. The device of claim 10, wherein the device has a first extended position wherein a first length of the inner hollow needle member extends beyond the distal end of the hollow catheter.

14. The device of claim 13, wherein the device has it second extended position wherein a second length of the inner hollow needle member extends beyond the distal end of the hollow catheter, wherein the second length is longer than the first length.

15. The device of claim 14, further comprising:
a hard tip rigidly fixed to the distal end of the catheter, the tip including a bearing surface on the proximal end thereof.

16. The device of claim 15, wherein the outer hollow needle member comprises a limiting member rigidly associated therewith and contacting the bearing surface of the tip member in the first and second extended positions.

17. A medical device, comprising:
a leur lock member including first and second grippable cap members, wherein the leur lock member is connectable to an aspirating device;
an outer tubular member having proximal and distal ends, the proximal end being connected to the leur lock member;
a rigid inner tubular member having proximal and distal ends and being slidably positioned within the proximal end of the outer tubular member, wherein the, proximal end of the inner tubular member is attached to the first grippable cap member;
an elongated stylet having proximal and distal ends and being slidably positioned within the rigid inner tubular member, wherein the proximal end of the stylet is attached to the second grippable cap member;
a compressable spring member having proximal and distal ends and coaxially surrounding a portion of the stylet, wherein the proximal end of the spring member is attached to the stylet;
an outer hollow needle member having a proximal end which is attached to the distal end of the spring member; and
an inner hollow needle member having proximal and distal ends and being telescopically received within the outer hollow needle member, wherein the inner hollow needle member is attached to the distal end of the stylet.

18. The device of claim 17, wherein the device includes a refracted position wherein the outer and inner hollow needle members are housed within the outer tubular member; a first extended position, wherein a first portion of the inner hollow needle member extends distally beyond the distal end of the outer tubular member; and a second extended position, wherein a second portion of the inner hollow needle member extends distally beyond the distal end of the outer tubular member, the second portion being longer than the first portion.

19. The device of claim 18, where the spring member is more compressed in the second extended position than in the first extended position.

20. The device of claim 17, further comprising:
a rigid fixed tubular member having proximal and distal ends and coaxially received within the outer tubular member, wherein the proximal end of the fixed tubular member is attached to the leur lock member, and wherein the fixed tubular member coaxially houses a portion of the inner tubular member and a portion of the stylet.

21. The device of claim 20, further comprising:
a limiting member fixed to the inner tubular member, wherein the limiting member biasly acts against the distal end of the fixed tubular member to prevent removal of the inner tubular member from the medical device.

22. The device of claim 21, wherein the stylet includes a kink which biasly acts against the distal end of the inner tubular member to prevent the removal of the stylet from the medical device.

23. The device of claim 18, wherein the spring member comprises a first spring having a first wavelength, and a second spring having a second wavelength, and wherein the first spring is oriented distally with respect to the second spring, and wherein the first wavelength is longer than the second wavelength while in the retracted and first extended positions.

24. The device of claim 18, wherein the spring member comprises a first spring having a first wavelength, and a second spring having a second wavelength, and wherein the first spring is oriented distally wit respect to the second spring, and wherein the first wavelength is shorter than the second wavelength while in the retracted and first extended positions.

25. The device of claim 24, wherein the first spring is integral with the second spring.

* * * * *